US011293934B2

(12) United States Patent
Ishida et al.

(10) Patent No.: US 11,293,934 B2
(45) Date of Patent: Apr. 5, 2022

(54) AUTOMATIC ANALYZER

(71) Applicants: HITACHI HIGH-TECHNOLOGIES CORPORATION, Tokyo (JP); ROCHE DIAGNOSTICS OPERATIONS INC., Indianapolis, IN (US)

(72) Inventors: Takeshi Ishida, Tokyo (JP); Sakuichiro Adachi, Tokyo (JP); Yoshihiro Yamashita, Tokyo (JP); Shunichirou Nobuki, Tokyo (JP); Hisashi Yabutani, Tokyo (JP); Isao Yamazaki, Tokyo (JP); Michaela Windfuhr, Iffeldorf (DE); Bernhard Hauptmann, Penzberg (DE); Simon Kuester, Krailling (DE)

(73) Assignees: Hitachi High-Tech Corporation, Tokyo (JP); Roche Diagnostics Operations, Inc., Indianapolis, IN (US)

( * ) Notice: Subject to any disclaimer, the term of this patent is extended or adjusted under 35 U.S.C. 154(b) by 299 days.

(21) Appl. No.: 16/307,787

(22) PCT Filed: Apr. 24, 2017

(86) PCT No.: PCT/JP2017/016151
§ 371 (c)(1),
(2) Date: Dec. 6, 2018

(87) PCT Pub. No.: WO2017/212808
PCT Pub. Date: Dec. 14, 2017

(65) Prior Publication Data
US 2019/0310275 A1    Oct. 10, 2019

(30) Foreign Application Priority Data
Jun. 9, 2016    (JP) .............................. JP2016-114924

(51) Int. Cl.
*A61L 2/10* (2006.01)
*A61L 2/24* (2006.01)
(Continued)

(52) U.S. Cl.
CPC .......... *G01N 35/00663* (2013.01); *A61L 2/10* (2013.01); *A61L 2/24* (2013.01);
(Continued)

(58) Field of Classification Search
None
See application file for complete search history.

(56) References Cited

U.S. PATENT DOCUMENTS 5,133,932 A    7/1992    Gunn et al.
6,030,578 A *  2/2000    McDonald ................ A61L 2/10
                                                    422/24
(Continued)

FOREIGN PATENT DOCUMENTS

CN    1450916 A    10/2003
CN    1978333 A    6/2007
(Continued)

OTHER PUBLICATIONS

Extended European Search Report issued in counterpart European Application No. 17809990.9 dated Dec. 18, 2019 (nine (9) pages).
(Continued)

*Primary Examiner* — Neil N Turk
(74) *Attorney, Agent, or Firm* — Crowell & Moring LLP

(57) ABSTRACT

An automatic analyzer is equipped with a sterilization mechanism removably attached to an opening of a container that holds a reagent and having an ultraviolet light generation section that radiates ultraviolet light; a suction nozzle removably attached, together with the sterilization mechanism, to the opening of the container; an analysis section adding the reagent drawn in by suction from the container
(Continued)

via the suction nozzle to the reagent, and executing an analysis operation; and a control section exercising variable control over an irradiation light intensity of the ultraviolet light generated by the ultraviolet light generation section.

12 Claims, 9 Drawing Sheets

(51) Int. Cl.
*A61L 2/26* (2006.01)
*G01N 35/10* (2006.01)
*G01N 35/00* (2006.01)
*C02F 1/32* (2006.01)

(52) U.S. Cl.
CPC ................................. *A61L 2/26* (2013.01); *C02F 1/32* (2013.01); *G01N 35/00* (2013.01); *G01N 35/00722* (2013.01); *G01N 35/1016* (2013.01); *A61L 2202/14* (2013.01); *G01N 2035/00673* (2013.01); *G01N 2035/00891* (2013.01); *G01N 2035/1023* (2013.01); *G01N 2035/1025* (2013.01)

(56) References Cited

U.S. PATENT DOCUMENTS

| | | | |
|---|---|---|---|
| 6,579,495 | B1 | 6/2003 | Maiden |
| 8,754,385 | B1* | 6/2014 | Gutman .................. A61L 2/24 250/455.11 |
| 2003/0035751 | A1 | 2/2003 | Hanley et al. |
| 2008/0035581 | A1 | 2/2008 | Kuhlmann et al. |
| 2009/0196802 | A1 | 8/2009 | Streppel |
| 2009/0250626 | A1 | 10/2009 | Schlesser et al. |
| 2012/0295301 | A1 | 11/2012 | Miyashita et al. |
| 2014/0084179 | A1* | 3/2014 | Ben-Hur ............... A61L 2/0047 250/429 |
| 2015/0284266 | A1 | 10/2015 | Matsui |
| 2016/0107904 | A1 | 4/2016 | Rajagopalan et al. |

FOREIGN PATENT DOCUMENTS

| | | | |
|---|---|---|---|
| CN | 101734751 | A | 6/2010 |
| CN | 102243244 | A | 11/2011 |
| CN | 103207284 | A | 7/2013 |
| CN | 105228956 | A | 1/2016 |
| JP | 52-7962 | | 1/1977 |
| JP | 63-163168 | A | 7/1988 |
| JP | 3-503730 | A | 8/1991 |
| JP | 8-117742 | A | 5/1996 |
| JP | 10-216711 | A | 8/1998 |
| JP | 2001-247108 | A | 9/2001 |
| JP | 2007-7083 | A | 1/2007 |
| JP | 2011-147362 | A | 8/2011 |
| JP | 2013-75257 | A | 4/2013 |
| JP | 2013-134141 | A | 7/2013 |
| JP | 2014-87544 | A | 5/2014 |
| JP | 2014-126415 | A | 7/2014 |
| JP | 2016-78895 | A | 5/2016 |
| WO | WO 2010-104225 | A1 | 9/2010 |
| WO | WO 2015/042657 | A1 | 4/2015 |

OTHER PUBLICATIONS

International Search Report (PCT/ISA/210) issued in PCT Application No. PCT/JP2017/016151 dated Jul. 18, 2017 with English translation (four (4) pages).
Japanese-language Written Opinion (PCT/ISA/237) issued in PCT Application No. PCT/JP2017/016151 dated Jul. 18, 2017 (four (4) pages).
Chinese-language Office Action issued in Chinese Application No. 201780034514.0 dated Jul. 2, 2021 (10 pages).

* cited by examiner

EMBODIMENT

COMPARISON

AUTOMATIC ANALYZER

TECHNICAL FIELD

The present disclosure relates to an automatic analyzer.

BACKGROUND ART

As an automatic analyzer, there is known an automatic analyzer that executes an analysis operation by adding a reagent to a specimen (hereinafter, referred to as "sample") to be analyzed and that derives an analysis result. Normally, the reagent is provided to a user in a state of being contained in a reagent container. The user installs the provided reagent container within or near the automatic analyzer and inserts a suction nozzle into an opening of the reagent container. The automatic analyzer draws in the reagent by suction from the reagent container through the suction nozzle to add the reagent to the sample, and measures a concentration of a substance to be measured contained in the sample.

In a case in which the reagent container becomes empty of the reagent, the user pulls out the suction nozzle from the reagent container and washes or cleans the suction nozzle as needed. The user then replaces the empty reagent container with a new reagent container filled with a reagent, inserts the suction nozzle into the new reagent container, and resumes an analysis operation.

Meanwhile, in reagent container replacement work, there is a probability that microorganisms are mixed into the reagent and the microorganisms grow. In a case of the growth of the microorganisms, there is a probability that properties of the reagent change to make it impossible to accurately determine the concentration of the substance to be measured contained in the sample or a probability of reduction in the reproducibility of an analysis result. Patent Document 1 describes a sterilization container that can kill microbes contained in a liquid within a container by irradiation of the liquid with ultraviolet light.

PRIOR ART DOCUMENT

Patent Document

Patent Document 1: JP-2013-75257-A

SUMMARY OF THE INVENTION

Problems to be Solved by the Invention

Meanwhile, in a case of sterilization of an object with ultraviolet light, it is necessary to appropriately select an irradiation light intensity to prevent a shortfall or an excess in the irradiation light intensity. For example, in a case of sterilizing the reagent in the reagent container with the ultraviolet light, there is a probability that the shortfall in the irradiation light intensity causes the insufficient killing of microorganisms and the growth of the microorganisms to thereby change the properties of the reagent. There is, on the other hand, a probability that the excess in the irradiation light intensity causes decomposition of or change in reagent components by the ultraviolet light to change the properties of the reagent similarly to the case of the shortfall.

Owing to this, with a sterilization scheme using the ultraviolet light, it is necessary to appropriately select the irradiation intensity of ultraviolet light so that the change in the properties of the reagent may fall within an allowable range. However, the sterilization container described in Patent Document 1 does not take into account the change in the properties of the reagent due to the excess or shortfall in the irradiation light intensity of the ultraviolet light.

An appropriate irradiation light intensity varies depending on a remaining amount of the reagent in the reagent container, and it is necessary to make lower the irradiation light intensity as the remaining amount of the reagent is smaller. However, the sterilization container described in Patent Document 1 does not exercise control over the irradiation light intensity in response to the remaining amount of the reagent. Owing to this, in the sterilization container described in Patent Document 1, the irradiation light intensity tends to become more excessive as the remaining amount of the reagent is smaller.

Furthermore, to sterilize the reagent using the sterilization container described in Patent Document 1, it is necessary to transfer the reagent from the reagent container to the sterilization container. However, the scheme described in Patent Document 1 and required to carry out transfer work generates both increasing concern that a new reagent is contaminated with the residual reagent and increasing concern that the reagent contacts the air and microorganisms are mixed into the reagent during the transfer work; thus, the properties of the reagent possibly change. In addition, long work time is necessary for the reagent transfer, compared with a scheme of replacement of the reagent container.

The present invention, therefore, provides a framework that can achieve both the sterilization of a reagent and the inhibition of change in properties of the reagent.

Means for Solving the Problems

To solve the problems, the present invention adopts a configuration set forth in, for example, claims. While the present specification includes a plurality of means for solving the problems, an example of the means is an "automatic analyzer including: a sterilization mechanism removably attached to an opening of a container that holds a reagent and having an ultraviolet light generation section that radiates ultraviolet light; a suction nozzle removably attached, together with the sterilization mechanism, to the opening of the container; an analysis section adding the reagent drawn in by suction from the container via the suction nozzle to the reagent, and executing an analysis operation; and a control section exercising variable control over an irradiation light intensity of the ultraviolet light generated by the ultraviolet light generation section."

The present specification contains a disclosed content of Japanese Patent Application No. 2016-114924 that forms the basis for the right of priority of the present application.

Effect of the Invention

According to the present invention, it is possible to achieve both the sterilization of the reagent and the inhibition of change in properties of the reagent. Problems other than those described above, configurations, and effects will be readily apparent from the description of embodiments given below.

MODES FOR CARRYING OUT THE INVENTION

Modes for carrying out the present invention will be described hereinafter with reference to the drawings. It is noted that the modes for carrying out the present invention are not limited to embodiments described below and various modifications can be made within the scope of the technical concept of the present invention.

In the present specification, a term "reagent" is not limited to a reaction reagent that produces a reaction with a sample but the term is used in a broad sense that the reagent includes a diluent, a detergent, a buffer solution, and a surface-active agent that activates an interface between an object to be analyzed and the reaction reagent. In addition, in the present specification, an expression of "sterilization" or "making microbes extinct" is used to mean not only "killing microbes" but also "making microbes harmless." Furthermore, these expressions are used to mean not only annihilating bacteria and microbes but also reducing bacteria and microbes.

(1) First Embodiment

(1-1) Analyzer Configuration

Figure 1:
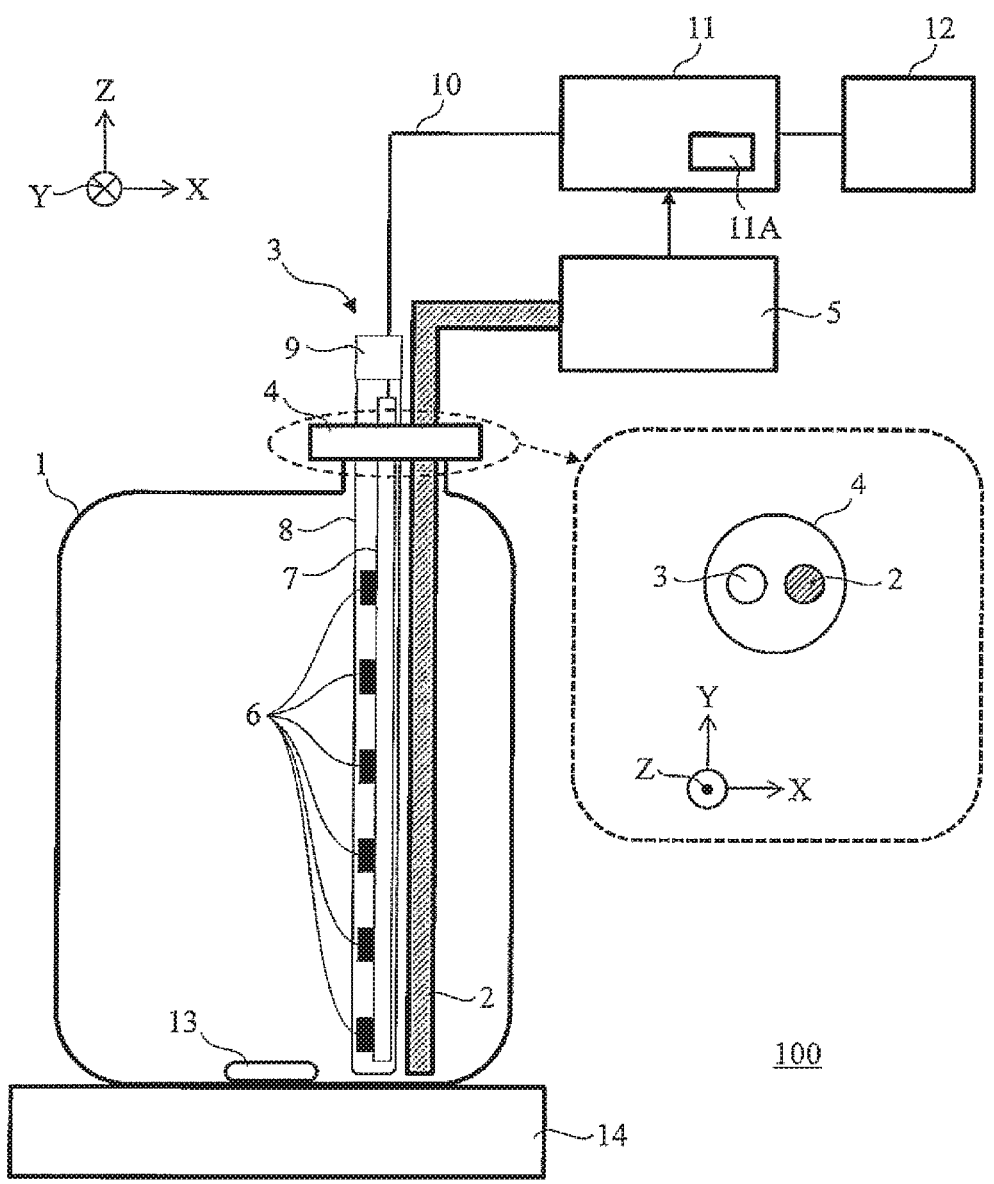
FIG. 1 is a diagram illustrating a schematic configuration of an automatic analyzer according to a first embodiment.

FIG. 1 illustrates a schematic configuration of an automatic analyzer 100 according to the present embodiment. The automatic analyzer 100 uses a reagent container 1 that is provided from a vendor and that is attached to an analyzer body. To this end, a user removes a cap attached to an opening of the reagent container 1 at a time of distribution from the opening thereof and inserts a suction nozzle 2 and a sterilization mechanism 3 into the exposed opening. The suction nozzle 2 and the sterilization mechanism 3 are fixed to a fixed section 4. The fixed section 4 is used as a new cap for the reagent container 1. Attaching the fixed section 4 to the opening of the reagent container 1 makes the reagent container 1 hermetically closed again. It is noted that the fixed section 4 is removable from the opening of the reagent container 1.

A reagent drawn in by suction from the suction nozzle 2 is supplied to an analysis section 5 and used for analysis. Description of known parts out of a configuration and processing functions of the analysis section 5 will be omitted. Functions characteristic of the present embodiment include a function to notify a control section 11 of a remaining amount of the reagent. The sterilization mechanism 3 is configured such that a substrate 7 mounting thereon a plurality of ultraviolet LEDs (Light Emitting Diodes) 6 is accommodated in a cylindrical accommodation section 8 having a closed bottom surface and yet an upper surface of the sterilization mechanism 3 is closed with a cap section 9.

It is noted that the number of ultraviolet LEDs 6 mounted on the substrate 7 is arbitrary and may be one. In the present embodiment, the six ultraviolet LEDs 6 are arranged equidistantly in a depth direction of the reagent container 1 (an extension direction of the accommodation section 8). However, disposition of the ultraviolet LEDs 6 may be determined depending on a shape and dimensions of the reagent container 1 attached to the analyzer body. In a case of FIG. 1, the ultraviolet LEDs 6 are attached to the substrate 7 in such a manner that the ultraviolet LEDs 6 radiate ultraviolet light only in an opposite direction to the suction nozzle 2. However, the ultraviolet LEDs 6 may be disposed on a side surface or the like of the substrate 7 in such a manner that the ultraviolet LEDs 6 can radiate ultraviolet light in a wider range. It is noted that a shape of the accommodation section 8 cut in parallel to a horizontal plane is arbitrary and may be rectangular or triangular.

An interconnection 10 is led out from an upper surface of the lid section 9 and connected to the control section 11. It is noted that the other end of the interconnection 10 is connected to the substrate 7 accommodated in the accommodation section 8. The control section 11 controls an irradiation light intensity by each of the ultraviolet LEDs 6 via the interconnection 10. The ultraviolet LEDs 6 act as a so-called ultraviolet light generation section and radiate ultraviolet light at wavelengths of 180 to 350 nm in a power feeding state. Suitable wavelengths of the ultraviolet light are such that sterilization efficiency is high against a bacterial strain to be sterilized and reagent components are difficult to decompose. More preferably, the ultraviolet light has wavelengths of 240 to 300 nm. Power is fed to the ultraviolet LEDs 6 through the interconnection 10. The control section 11 controls changeover between irradiation and turning off of the ultraviolet LEDs 6 depending on whether the power is fed to the ultraviolet LEDs 6, and controls illuminance of the ultraviolet light depending on a magnitude of the power fed thereto.

The accommodation section 8 has a function to protect the ultraviolet LEDs 6 and the substrate 7 from the reagent. In addition, the accommodation section 8 is formed with a material that transmits the ultraviolet light radiated from the ultraviolet LEDs 6. In the present embodiment, glass or resin that transmits ultraviolet light is used for the accommodation section 8. In a case of using quartz glass, ultraviolet light transmittance of the accommodation section 8 is equal to or higher than 90%. In this case, the accommodation section 8 can keep down the attenuation of the illuminance of the ultraviolet light and enhance the sterilization efficiency. Resin, which is lower than quartz glass in ultraviolet light transmittance, contributes to increasing a mechanical strength of the accommodation section 8, thus reducing a probability of falsely damaging the sterilization mechanism 3 at a time of replacement of the reagent container 1.

The control section 11 controls any of a current supplied to the ultraviolet LEDs 6, a voltage, and current-carrying time, or a combination thereof to an appropriate value on the basis of the remaining amount of the reagent of which the control section 11 is notified by the analysis section 5. The control section 11 here controls any of the current, the voltage, and the current-carrying time, or the combination thereof in such a manner that the irradiation light intensity of the ultraviolet light becomes smaller as the remaining amount of the reagent is smaller.

The illuminance of the generated ultraviolet light becomes higher as a current value or a voltage value is larger. In addition, the illuminance of the generated ultraviolet light becomes higher as the current-carrying time is longer. A length of the current-carrying time is variable depending on a length of a pulse width corresponding to the current-carrying time. As a result of these combined factors, the irradiation light intensity of the ultraviolet light changes. It is noted that the substrate 7 can assume part of or all of functions of the control section 11.

The control section 11 controls the current, the voltage, and the current-carrying time in such a manner that the irradiation light intensity of the generated ultraviolet light is equal to or higher than an irradiation light intensity of ultraviolet light per unit amount necessary for sterilization of the reagent and equal to or lower than an irradiation light intensity of ultraviolet light corresponding to an upper limit of an allowable range for change in properties of the reagent. The irradiation light intensity of the ultraviolet light per unit amount necessary for sterilization of the reagent differs depending on a bacterial strain to be sterilized and the wavelength of the ultraviolet light to be used. Owing to this, the irradiation light intensity of the ultraviolet light per unit amount necessary for sterilization of the reagent is obtained by measurement or calculation in advance for a combination of the bacterial strain to be sterilized and the wavelength of the ultraviolet light.

In addition, the irradiation light intensity of the ultraviolet light with which the change in the properties of the reagent falls within the allowable range differs depending on a combination of reagent components (chemically bonded species, in particular) and the wavelength of the ultraviolet light to be used. Owing to this, the irradiation light intensity of the ultraviolet light per unit amount necessary for sterilization of the reagent is obtained by measurement or calculation in advance for the combination of the reagent components and the wavelength of the ultraviolet light. A storage section 11A of the control section 11 also stores relationships between these relationships and the remaining amount of the reagent (tables). Needless to say, the relationships between these relationships and the remaining amount of the reagent are also obtained by measurement or calculation in advance.

The analysis section 5 calculates the remaining amount of the reagent within the reagent container 1 from a value of the number of analyses (or number of measurements). An amount of the reagent used per analysis (or per measurement) is known in advance; thus, multiplying the value of the amount of the reagent by the number of analyses (or number of measurements) makes it possible to calculate a used amount after replacement of the reagent container 1. In addition, an amount of the reagent filled in the new reagent container 1 is also known; thus, subtracting the calculated used amount from the known amount makes it possible to obtain the remaining amount. It is noted that the remaining amount of the reagent can be also obtained using a reagent liquid level detection mechanism mounted in the analysis section 5. Since the liquid level detection mechanism is known, detailed description thereof will be omitted.

In the meantime, the automatic analyzer 100 has a magnetic stirrer 14 disposed as a mounting table on which the reagent container 1 is mounted. The magnetic stirrer 14 configures, together with a stirrer 13 loaded into the reagent container 1, a stirring mechanism, rotates the stirrer 13 using a magnetic force, and stirs the reagent. Stirring the reagent enables uniform sterilization of the reagent. It is noted that the stirring mechanism may be a stirring blade or may be designed to repeat suction and delivery of the reagent by the suction nozzle 2. Alternatively, the stirring mechanism may be designed to use convection of the reagent produced by heat generated from the ultraviolet LEDs 6 disposed locally on a bottom side of the reagent container 1.

The interconnection 10 includes not only an interconnection for feeding and controlling the ultraviolet LEDs 6 but also a signal line for a temperature sensor such as a thermistor and a signal line for notifying the control section 11 of states of the ultraviolet LEDs 6. Furthermore, the automatic analyzer 100 has a display section 12 that notifies a user of execution of appropriate reagent sterilization or detection of an abnormality. The user of the analyzer can grasp states of the reagent and the sterilization mechanism through a screen displayed on the display section 12. It is noted that an interface used to operate or control the automatic analyzer 100, the analysis result, an analyzer state may be displayed on the display section 12. Contents of notification include, for example, whether the appropriate sterilization has been executed and detection of the abnormality.

(1-2) Effects

Using the automatic analyzer 100 described above enables appropriate control over the irradiation intensity of the ultraviolet light used to sterilize the reagent in response to the amount of the reagent remaining in the reagent container 1. Specifically, the control section 11 can reduce the irradiation light intensity of the ultraviolet light so that the irradiation light intensity is a proper intensity with a reduction in the remaining amount of the reagent.

Figure 2A:
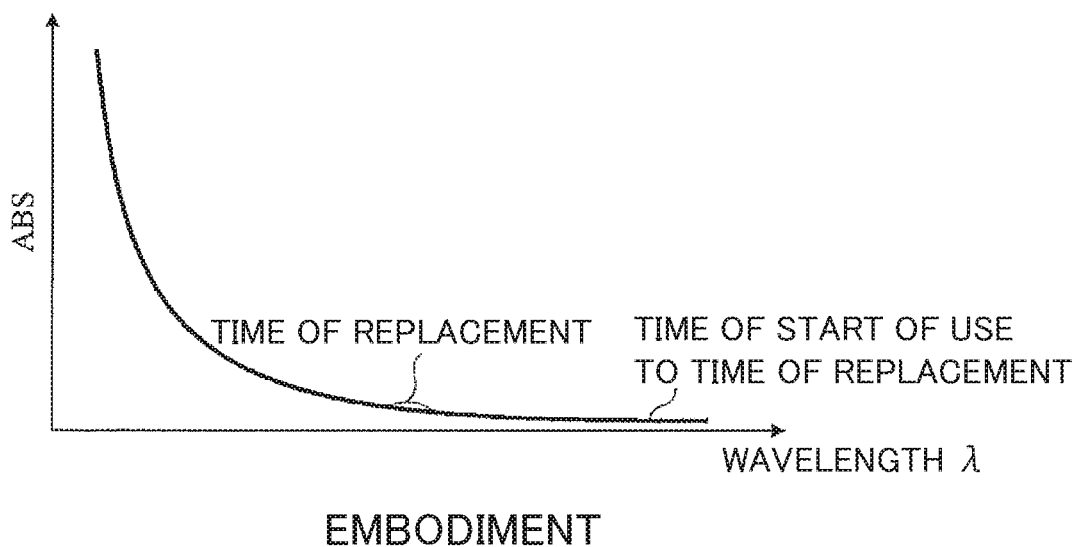
FIG. 2A is an illustrative diagram of time change in a case of measuring absorbance using the automatic analyzer according to the first embodiment.

Adopting this control scheme makes it possible to achieve both inhibition of the change in the properties of the reagent due to the growth of microorganisms in the reagent caused by a shortfall in the irradiation light intensity or due to an excess in the irradiation light intensity and the sterilization of the reagent as well as maintaining the reagent components. FIG. 2A illustrates a time change in a measurement result of absorbance according to the present embodiment. In FIG. 2A a vertical axis indicates the absorbance and a horizontal axis indicates the wavelength. As depicted in FIG. 2A, a measured value of the absorbance hardly changes at any wavelength from the time of start of use of the reagent container 1 to the time of replacement.

Figure 2B:
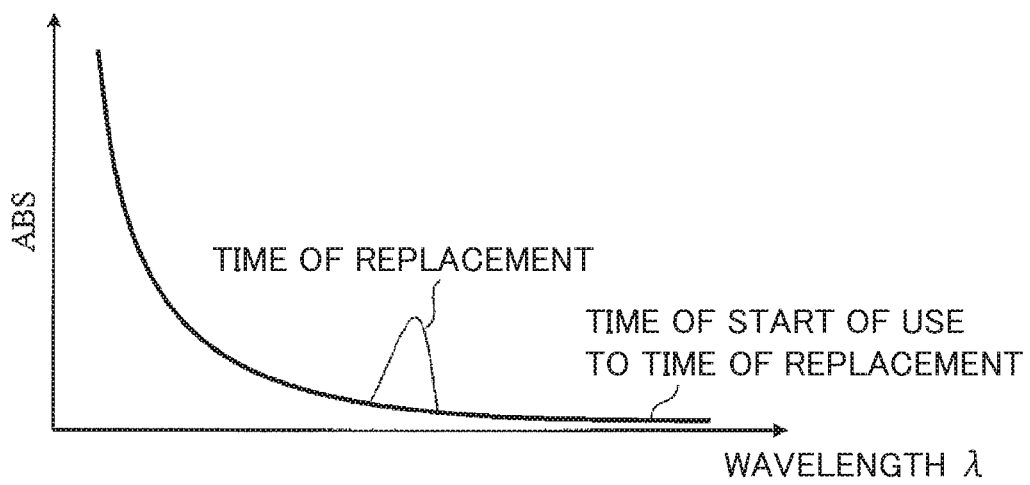
FIG. 2B is an illustrative diagram of time change in a case of measuring absorbance using an automatic analyzer according to a comparison.

In FIG. 2A, there is change, that is, a slight increase in the absorbance at a certain wavelength determined by the reagent components and the wavelength of the ultraviolet light. The change is, however, very small, which indicates that the properties of the reagent is maintained. FIG. 2B illustrates time change in a measurement result of absorbance in a case of using the ultraviolet light for sterilization with a light intensity of the ultraviolet light kept constant (comparison). In a case of keeping constant the light intensity of the ultraviolet light irrespectively of the remaining amount of the reagent, the absorbance greatly increases at the certain wavelength described above as time is closer to the time of replacement of the reagent container 1. This increase in the absorbance results from decomposition of or change in the reagent components, and the properties of the reagent have greater change as an increase amount of the absorbance is higher.

As described so far, appropriately controlling the irradiation light intensity (that is, illuminance and irradiation time) of the ultraviolet light used for the sterilization of the reagent on the basis of the remaining amount of the reagent makes it possible to achieve both sterilization and keeping of the reagent components and to achieve a longer-term use of the reagent.

Moreover, in the automatic analyzer 100 according to the present embodiment, the sterilization mechanism 3 is removably attached to the reagent container 1 provided from the vendor; thus, reagent transfer work is unnecessary at a time of replacement of the reagent. In addition, there is no concern of mixture of the residual reagent or microorganisms as seen in the case of transfer of the reagent.

Furthermore, at a time of replacement of the reagent container 1, it is only required to pull out the sterilization mechanism 3 as well as the suction nozzle 2, to wash or clean the sterilization mechanism 3 as well as the suction nozzle 2 as needed, and to insert the sterilization mechanism 3 as well as the suction nozzle 2 into the new reagent container 1. Owing to this, convenience of operations by insertion of the sterilization mechanism 3 into the reagent container 1 is almost the same as operations in a case of not inserting the sterilization mechanism 3 into the reagent container 1. Furthermore, it is possible to eliminate or mitigate the concern of change in the properties of the reagent due to the mixture of the residual reagent or microorganisms or contact with the air occurring at the time of transfer of the reagent into the sterilization container (Patent Document 1).

(2) Second Embodiment

In the present embodiment, a case of assigning measures against heat generation from the ultraviolet LEDs 6 to the automatic analyzer 100 described above will be described. As is known, the ultraviolet LEDs 6 generate heat when radiating ultraviolet light. Excess of a junction temperature of the ultraviolet LEDs 6 over absolute maximum rating specified by specifications constitutes a factor for shortening lives of the ultraviolet LEDs 6 and a factor for a failure.

The heat from the ultraviolet LEDs 6 is emitted not only into the reagent but also to outside of the reagent through the substrate 7, the accommodation section 8, and the interconnection 10. If the remaining amount of the reagent decreases with an increase in the number of experiments (number of measurements), it is difficult for the ultraviolet LEDs located at higher positions than a liquid level of the reagent to emit the heat into the reagent. Owing to this, the ultraviolet LEDs 6 at the higher positions than the liquid level of the reagent tend to be higher in junction temperature and shorter in life than the ultraviolet LEDs at lower positions than the liquid level of the reagent.

To address the problem, therefore, a function to selectively turn off the ultraviolet LEDs 6 located at the higher positions than the liquid level of the reagent or reduce light intensities of the ultraviolet light from the ultraviolet LEDs 6 on the basis of the remaining amount of the reagent is mounted in the control section 11 of the present embodiment. It is assumed that the positions of the ultraviolet LEDs 6 mounted on the substrate 7 are stored in the storage section 11A of the control section 11. Mounting this function in the control section 11 makes it possible to effectively prevent shortening of the lives and a failure of the ultraviolet LEDs 6 located at relatively high positions and to extend a life of the sterilization mechanism 3.

(3) Third Embodiment

In the second embodiment described above, the ultraviolet LEDs 6 located at the higher positions than the liquid level of the reagent are selectively turned off or the light intensities of the ultraviolet light from the ultraviolet LEDs 6 are reduced to take measures against the heat generation from the ultraviolet LEDs 6. In the present embodiment, the following function is provided in the control section 11 as an alternative to or in addition to the function of the second embodiment.

In the present embodiment, a temperature sensor such as a thermistor is disposed near the ultraviolet LEDs 6 on the substrate 7. The temperature sensor may be provided per ultraviolet LED 6 on one-to-one basis or a plurality of temperature sensors may be provided at positions that are not necessarily on one-to-one basis for the ultraviolet LEDs 6. The control section 11 is notified of a measurement result of the temperature sensor through the substrate 7 and the interconnection 10.

The control section 11 controls any of the current supplied to the ultraviolet LEDs 6, the voltage, the current-carrying time or the combination thereof in such a manner that the junction temperature of the ultraviolet LEDs 6 measured indirectly through the temperature sensor does not exceed a predetermined value. It is thereby possible to avoid a situation in which the lives of the ultraviolet LEDs located at the lower positions than the liquid level of the reagent become shorter than assumed and to prevent occurrence of a failure. It is noted that the control section 11 may control the ultraviolet LEDs 6 one by one or in present groups.

(4) Fourth Embodiment

Figure 3:
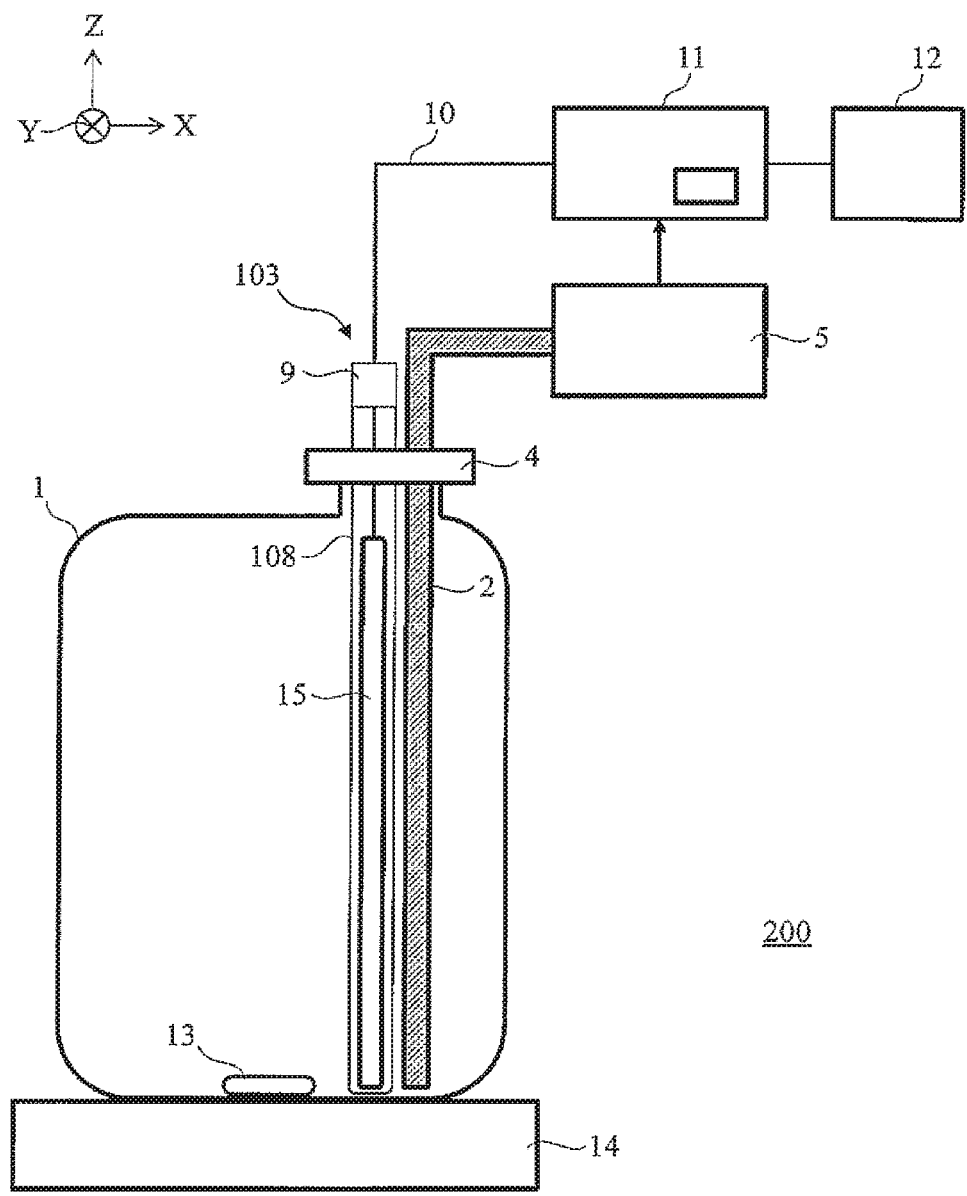
FIG. 3 is a diagram illustrating a schematic configuration of an automatic analyzer according to a fourth embodiment.

FIG. 3 illustrates a schematic configuration of an automatic analyzer 200 according to a fourth embodiment. In FIG. 3, corresponding sections to those in FIG. 1 are denoted by same or corresponding reference characters. The automatic analyzer 200 uses a sterilization mechanism 103 as an alternative to the sterilization mechanism 3.

The sterilization mechanism 103 differs from the sterilization mechanism 3 in the use of an ultraviolet lamp 15 as the ultraviolet light generation section and the use of an accommodation section 108. As the ultraviolet lamp 15, a low-pressure mercury lamp or a high-pressure mercury lamp is used. The low-pressure mercury lamp mainly radiates ultraviolet light including one at a wavelength of 254 nm that is high in sterilization efficiency and one at a wavelength of 185 nm that generates ozone. The low-pressure mercury lamp cuts off or transmits the ultraviolet light at 185 nm depending on a type of glass that configures the ultraviolet lamp 15. On the other hand, while the high-pressure mercury lamp mainly radiates ultraviolet light at a wavelength of 365 that does not contribute to sterilization, the high-pressure mercury lamp also radiates ultraviolet light at 254 to 334 nm that contributes to sterilization. The ultraviolet lamp 15 is selected from the viewpoint of ensuring the high sterilization efficiency against the bacterial strain to be sterilized and including the wavelength suitable to make the reagent components difficult to decompose.

Glass or resin transmitting the ultraviolet light is used for the accommodation section 108. However, a function of an optical filter may be added to the accommodation section 108 to transmit only the ultraviolet light at an appropriate wavelength. The control section 11 controls any of the current supplied to the ultraviolet lamp 15, the voltage, and the current-carrying time or the combination thereof on the basis of the remaining amount of the reagent. In the present embodiment, similarly to the first embodiment, the control section 11 controls any of or some of the current, the voltage, and the current-carrying time in such a manner that the irradiation light intensity of the ultraviolet light becomes lower as the remaining amount of the reagent is smaller.

The control section 11 controls the current, the voltage, and the current-carrying time in such a manner that the irradiation light intensity of the generated ultraviolet light is equal to or higher than an irradiation light intensity of ultraviolet light per unit amount necessary for sterilization of the reagent and equal to or lower than an irradiation light intensity of ultraviolet light corresponding to an upper limit of an allowable range for change in properties of the reagent. The irradiation light intensity of the ultraviolet light per unit amount necessary for sterilization of the reagent differs depending on the bacterial strain to be sterilized and filter functions of the ultraviolet lamp 15 and the accommodation section 108 to be used. Owing to this, the irradiation light intensity of the ultraviolet light per unit amount necessary for sterilization of the reagent is obtained by measurement or calculation in advance for a combination of the bacterial strain to be sterilized and the filter functions of the ultraviolet lamp 15 and the accommodation section 108 to be used.

In addition, the irradiation light intensity of the ultraviolet light with which the change in the properties of the reagent falls within the allowable range differs depending on a combination of the reagent components (chemically bonded species, in particular) and the filter functions of the ultraviolet lamp 15 and the accommodation section 108. Owing to this, the irradiation light intensity of the ultraviolet light per unit amount necessary for sterilization of the reagent is obtained by measurement or calculation in advance for the combination of the bacterial strain to be sterilized and the filter functions of the ultraviolet lamp 15 and the accommodation section 108. The storage section 11A of the control section 11 stores relationships between these relationships and the remaining amount of the reagent (tables). Needless to say, the relationships between these relationships and the remaining amount of the reagent are also obtained by measurement or calculation in advance.

While a stirring mechanism similar to that of the first embodiment can be adopted in the present embodiment, the ultraviolet lamp 15 smaller than a depth of the reagent container 1 may be installed on the bottom side of the reagent container 1 and convection may be produced in the reagent by the heat generated by the ultraviolet lamp 15 to stir the reagent.

(5) Fifth Embodiment

Figure 4:
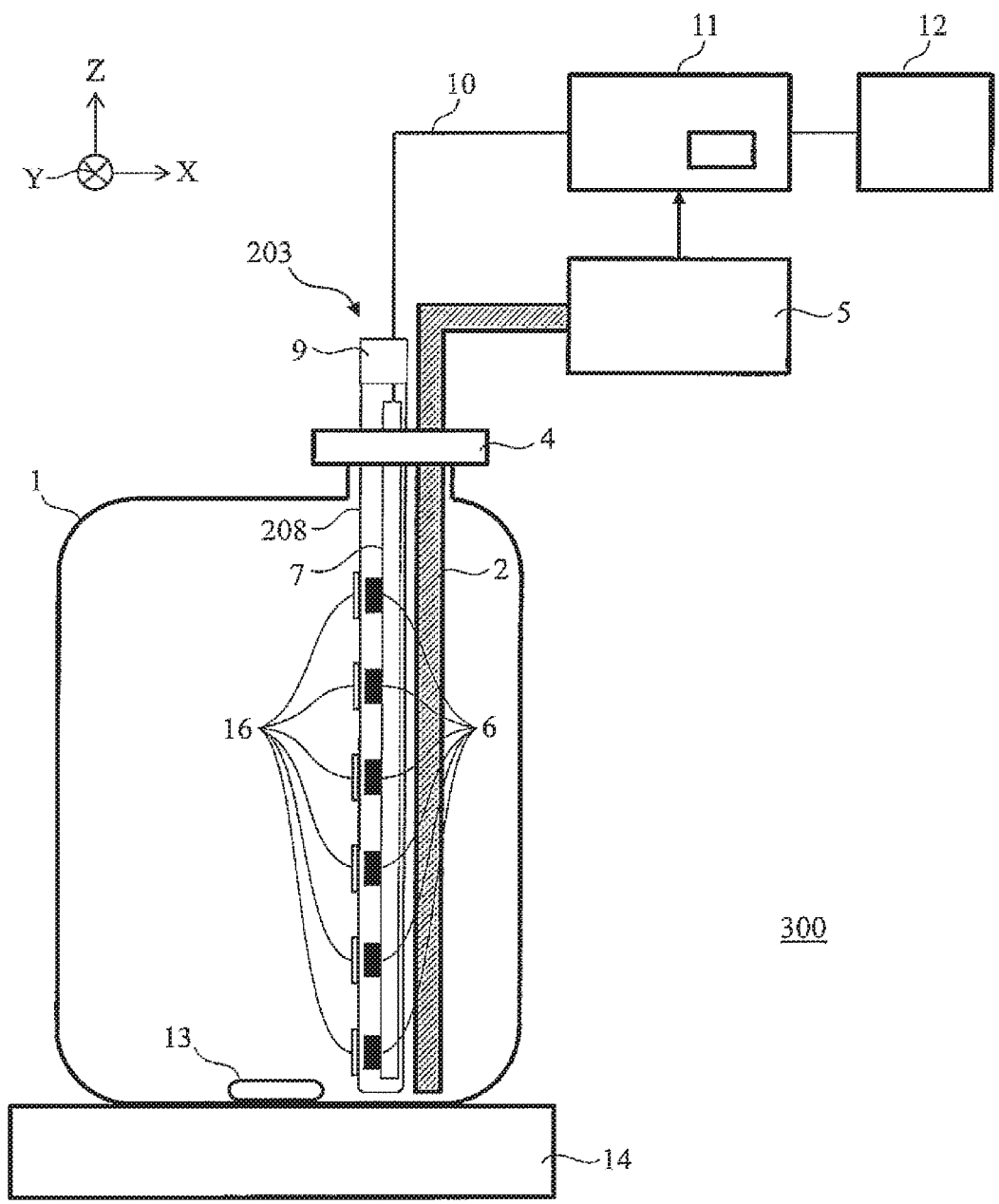
FIG. 4 is a diagram illustrating a schematic configuration of an automatic analyzer according to a fifth embodiment.

FIG. 4 illustrates a schematic configuration of an automatic analyzer 300 according to a fifth embodiment. In FIG. 4, corresponding sections to those in FIG. 1 are denoted by same or corresponding reference characters. The automatic analyzer 300 uses a sterilization mechanism 203 as an alternative to the sterilization mechanism 3.

The sterilization mechanism 203 is configured such that the substrate 7 mounting thereon the plurality of ultraviolet LEDs 6 is accommodated in an accommodation section 208. In a case of the present embodiment, the accommodation section 208 is formed with resin or metal, and opening portions that transmit ultraviolet light and windows 16 that block the opening portions are disposed at positions facing the ultraviolet LEDs 6 in the accommodation section 208. The windows 16 are, for example, glass. However, the accommodation section 208 may be formed with a material that transmits ultraviolet light or a material that does not transmit ultraviolet light. Using the resin or metal accommodation section 208 makes it possible to reduce a possibility of falsely damaging the sterilization mechanism 203 at a time of replacement of the reagent container 1.

It is noted that using the metal accommodation section 208 can improve heat dissipation performance, compared with using the resin accommodation section 208. Owing to this, in a case of using the metal accommodation section 208, it is possible to keep the junction temperature of the ultraviolet LEDs 6 in a range in which the junction temperature does not exceed the maximum absolute rating even with the ultraviolet LEDs 6 driven by a higher voltage or current than that applied in a case of the resin accommodation section 208. When the metal accommodation section 208 is used, however, the reagent tends to be warmed. It is, therefore, desirable to use the resin accommodation section 208 in a case in which warming of the reagent is to be suppressed.

The windows 16 are disposed to block the opening portions provided in region parts irradiated with the ultraviolet light radiated from the ultraviolet LEDs 6 in the accommodation section 208. The ultraviolet LEDs 6 and the substrate 7 are protected from the reagent since the windows 16 completely block the opening portions of the accommodation section 208. The ultraviolet light transmitted by the windows 16 is radiated to the reagent within the reagent container 1. In a case of using quartz glass for the windows 16, ultraviolet light transmittance is equal to or higher than 90%. In this case, sterilization efficiency can be enhanced because of less attenuation of the ultraviolet light illuminance.

(6) Sixth Embodiment

Figure 5:
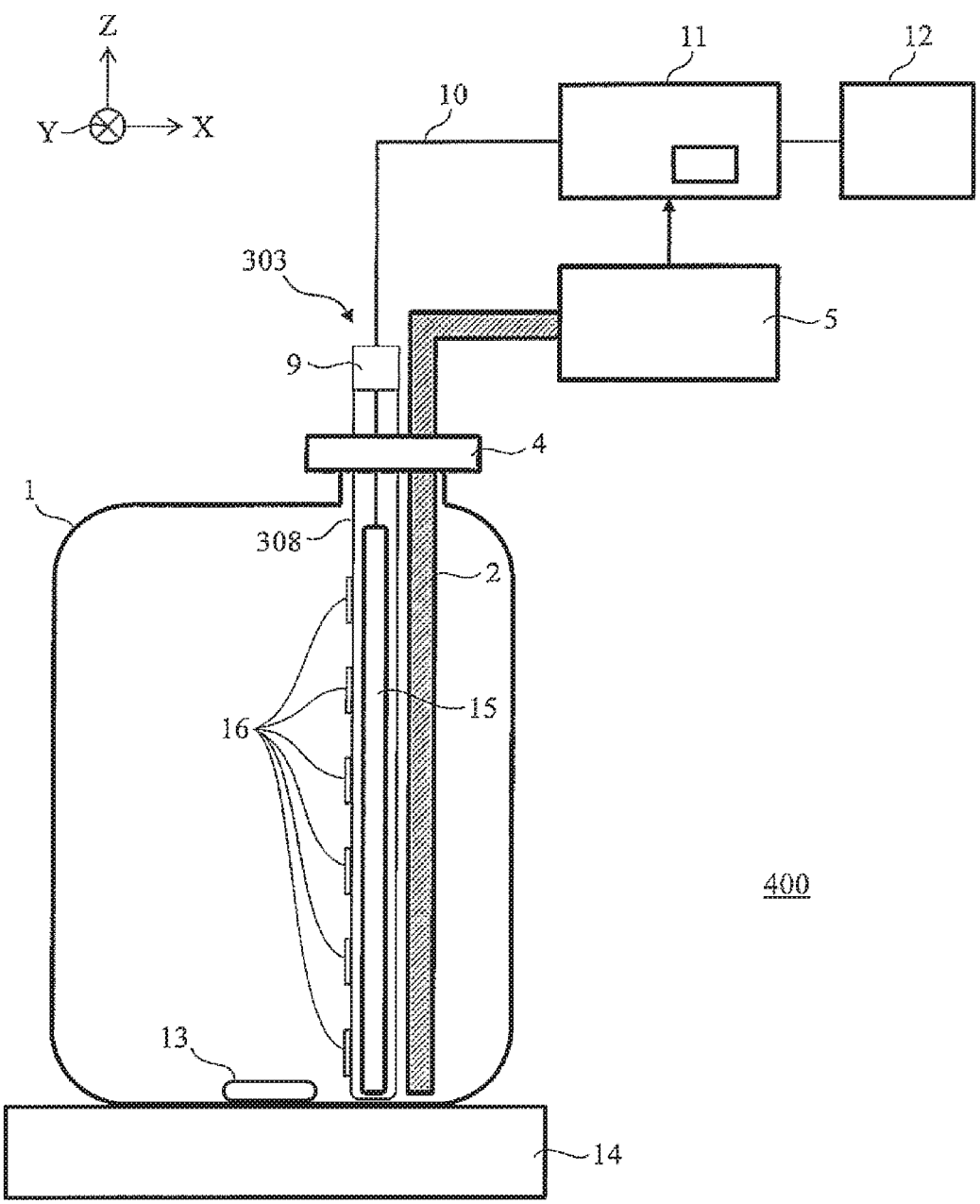
FIG. 5 is a diagram illustrating a schematic configuration of an automatic analyzer according to a sixth embodiment.

FIG. 5 illustrates a schematic configuration of an automatic analyzer 400 according to a sixth embodiment. In FIG. 5, corresponding sections to those in FIG. 3 are denoted by same or corresponding reference characters. The automatic analyzer 400 uses a sterilization mechanism 303 as an alternative to the sterilization mechanism 103.

The sterilization mechanism 303 is configured such that the ultraviolet lamp 15 is accommodated in an accommodation section 308. In a case of the present embodiment, the accommodation section 308 is formed with resin or metal, and the windows 16 that transmit ultraviolet light are disposed at positions facing the ultraviolet LEDs 6 in the accommodation section 308. The windows 16 are, for example, glass. However, a function of an optical filter may be added to the windows 16 to transmit only the ultraviolet light at an appropriate wavelength. The accommodation section 308 may be formed with a material that transmits ultraviolet light or a material that does not transmit ultraviolet light.

In a case of configuring the accommodation section 308 with the material that transmits ultraviolet light, a function of an optical filter may be added to the accommodation section 308 to transmit only the ultraviolet light at an appropriate wavelength. In addition, using the resin or metal accommodation section 308 makes it possible to reduce a possibility of falsely damaging the sterilization mechanism 303 at a time of replacement of the reagent container 1.

For information, the opening portions are provided in region parts irradiated with the ultraviolet light radiated from the ultraviolet LEDs 6 in the accommodation section 308, and the windows 16 are disposed to block the opening portions. The accommodation section 308 and the windows 16 protect the ultraviolet lamp 15 from the reagent. The ultraviolet light transmitted by the windows 16 is radiated to the reagent within the reagent container 1. The sterilization efficiency can be enhanced as the opening portions and the windows 16 are larger and the numbers of the opening portions and the windows 16 are larger. On the other hand, a mechanical strength of the accommodation section 308 declines as the opening portions and the windows 16 are larger and the numbers of the opening portions and the windows 16 are larger. Owing to this, it is desirable that a total area of the opening portions is equal to or smaller than half of a surface area of the accommodation section 308.

In a case of using quartz glass for the windows 16, ultraviolet light transmittance is equal to or higher than 90%. In this case, sterilization efficiency can be enhanced because of less attenuation of the ultraviolet light illuminance. The control section 11 controls any of the current supplied to the ultraviolet lamp 15, the voltage, and the current-carrying time or the combination thereof on the basis of the remaining amount of the reagent. In this case, the control section 11 exercises control in such a manner that the irradiation light intensity of the ultraviolet light generated from the ultraviolet lamp 15 is equal to or higher than the irradiation light intensity of ultraviolet light per unit amount necessary for sterilization of the reagent and equal to or lower than the irradiation light intensity of ultraviolet light corresponding to the upper limit of the allowable range for change in properties of the reagent.

The irradiation light intensity of the ultraviolet light per unit amount necessary for sterilization of the reagent differs depending on the bacterial strain to be sterilized and the filter functions of the ultraviolet lamp 15, the accommodation section 308, and the windows 16 to be used. Owing to this, the irradiation light intensity of the ultraviolet light per unit amount necessary for sterilization of the reagent is obtained by measurement or calculation in advance for a combination of the bacterial strain to be sterilized and the filter functions of the ultraviolet lamp 15, the accommodation section 308, and the windows 16 to be used.

In addition, the irradiation light intensity of the ultraviolet light with which the change in the properties of the reagent falls within the allowable range differs depending on a combination of the reagent components (chemically bonded species, in particular) and the filter functions of the ultraviolet lamp 15, the accommodation section 308, and the windows 16 to be used. Owing to this, the irradiation light intensity of the ultraviolet light per unit amount necessary for sterilization of the reagent is obtained by measurement or calculation in advance for the combination of the reagent components and the filter functions of the ultraviolet lamp 15, the accommodation section 308, and the windows 16 to be used.

(7) Seventh Embodiment

Figure 6:
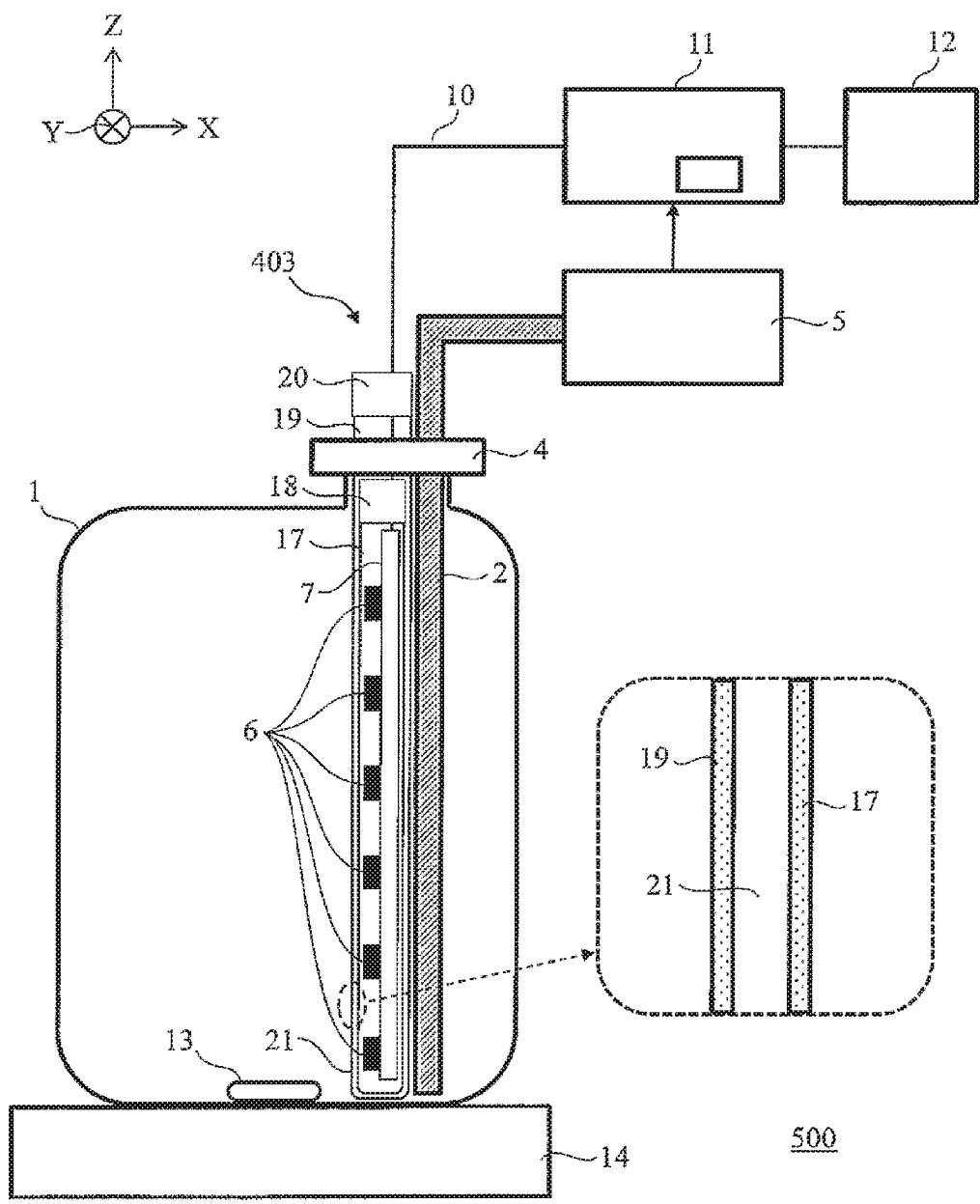
FIG. 6 is a diagram illustrating a schematic configuration of an automatic analyzer according to a seventh embodiment.

FIG. 6 illustrates a schematic configuration of an automatic analyzer 500 according to a seventh embodiment. In FIG. 6, corresponding sections to those in FIG. 1 are denoted by same or corresponding reference characters. The automatic analyzer 500 uses a sterilization mechanism 403 as an alternative to the sterilization mechanism 3.

The sterilization mechanism 403 is configured with a first accommodation section 17 that accommodates the substrate 7 mounting thereon the ultraviolet LEDs 6, a second accommodation section 19 that accommodates the first accommodation section 17 and a cap section 18 of the first accommodation section 17, a cap section 20 of the second accommodation section 19, and an adiabatic section 21. The first accommodation section 17 is hermetically closed by the cap section 18 through which the interconnection 10 penetrates. The second accommodation section 19 is hermetically closed by the cap section 20 through which the interconnection 10 penetrates. The adiabatic section 21 is disposed between the first accommodation section 17 and the second accommodation section 19.

Glass or resin that transmits ultraviolet light is used for the first accommodation section 17 and the second accommodation section 19. In a case of using quartz glass, sterilization efficiency can be enhanced because of less attenuation of the ultraviolet light illuminance. On the other hand, in a case of using resin, ultraviolet light transmittance is lower than that of quartz glass but the mechanical strength can be enhanced. In a case of forming the second accommodation section 19 with resin, in particular, a probability of falsely damaging the sterilization mechanism 403 at a time of replacement of the reagent container 1 is reduced.

The adiabatic section 21 is formed with air, resin, rubber, and the like and thermal conductivity thereof is equal to or lower than 0.5 W/(m·K). The adiabatic section 21 separates the first accommodation section 17 from the second accommodation section 19 (does not bring the first accommodation section 17 and the second accommodation section 19 into direct contact with each other). Presence of the adiabatic section 21 makes it possible to suppress or reduce conduction of heat, which is generated when the ultraviolet LEDs 6 radiate ultraviolet light, to the reagent and to suppress or reduce warming of the reagent.

Needless to say, the adiabatic section 21 is disposed in portions except for regions irradiated with the ultraviolet light in such a manner that the adiabatic section 21 does not obstruct irradiation of the ultraviolet light. The automatic analyzer 500 configured in this way can suppress or reduce a probability of the change in the properties of the reagent due to the warming of the reagent accompanying the irradiation of the ultraviolet light, compared with the automatic analyzer 100.

(8) Eighth Embodiment

Figure 7:
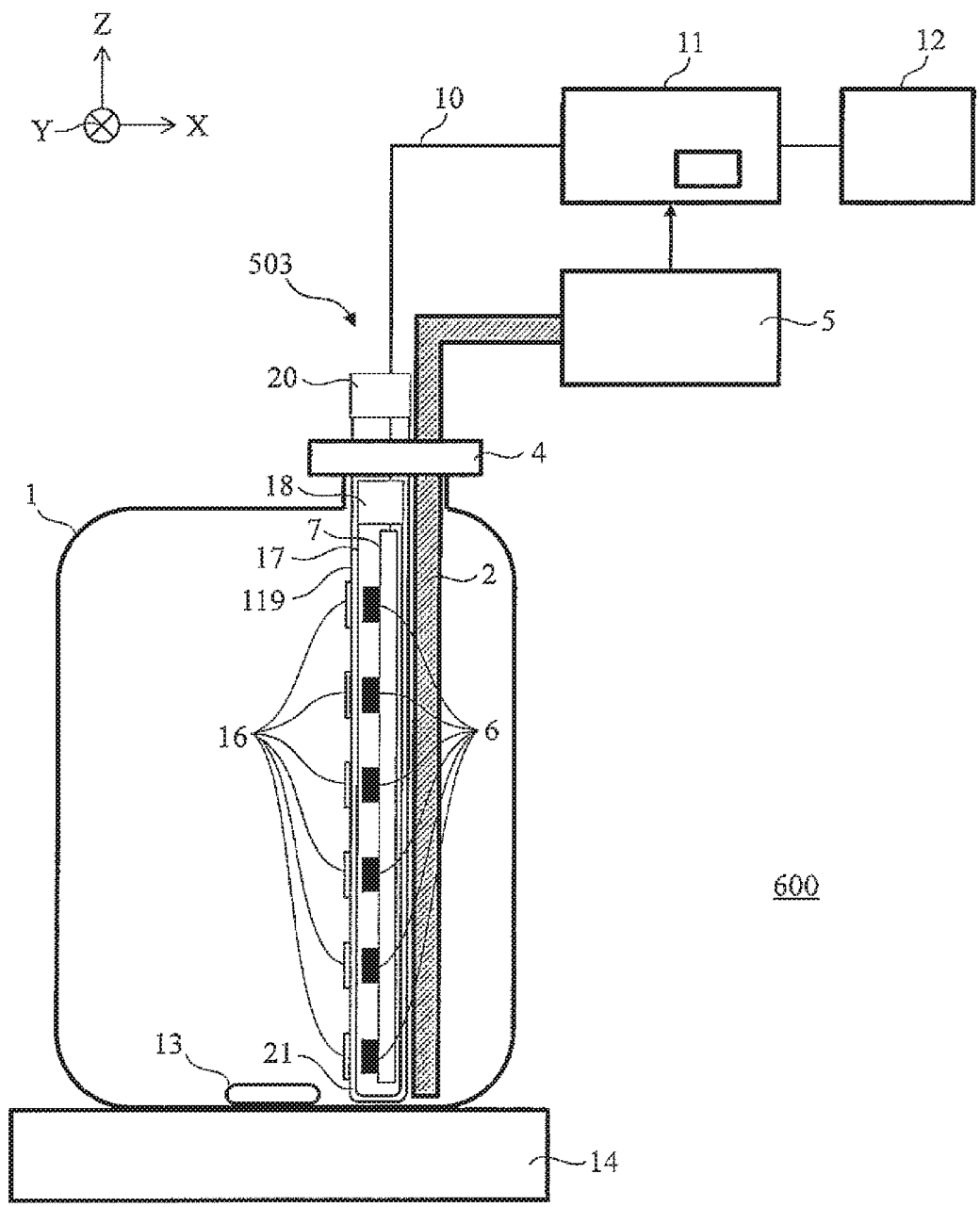
FIG. 7 is a diagram illustrating a schematic configuration of an automatic analyzer according to an eighth embodiment.

FIG. 7 illustrates a schematic configuration of an automatic analyzer 600 according to an eighth embodiment. In FIG. 7, corresponding sections to those in FIGS. 4 and 6 are denoted by same or corresponding reference characters. The automatic analyzer 600 uses a sterilization mechanism 503.

The sterilization mechanism 503 is configured with the first accommodation section 17 that accommodates the substrate 7 mounting thereon the ultraviolet LEDs 6, a second accommodation section 119 that accommodates the first accommodation section 17 and the cap section 18 of the first accommodation section 17, the cap section 20 of the second accommodation section 119, and the adiabatic section 21. This double-pipe structure is similar to that of the seventh embodiment. Needless to say, the cap section 18 through which the interconnection 10 penetrates hermetically closes the first accommodation section 17, and the cap section 20 through which the interconnection 10 penetrates hermetically closes the second accommodation section 119.

It is noted, however, that the opening portions are formed at positions facing the ultraviolet LEDs 6 (regions irradiated with the ultraviolet region) in the second accommodation section 119, and the opening portions are blocked by the windows 16. This second accommodation section 119 and the windows 16 protect the first accommodation section 17 from the reagent. Needless to say, the windows 16 transmit the ultraviolet light.

The first accommodation section 17 is configured with glass or resin that transmits ultraviolet light. The second accommodation section 119 is configured with resin or metal. The windows 16 are configured with glass that transmits ultraviolet light. The second accommodation section 119 may be formed with a material that transmits ultraviolet light or a material that does not transmit ultraviolet light. Forming the second accommodation section 119 with resin or metal makes it possible to reduce a possibility of falsely damaging the sterilization mechanism 503 at a time of replacement of the reagent container 1.

In a case of using quartz glass for the first accommodation section 17 and the windows 16, sterilization efficiency can be enhanced because of less attenuation of the ultraviolet light illuminance. The automatic analyzer 600 configured in this way can suppress or reduce a probability of the change in the properties of the reagent due to the warming of the reagent accompanying the irradiation of the ultraviolet light, compared with the automatic analyzer 100.

(9) Ninth Embodiment

Figure 8:
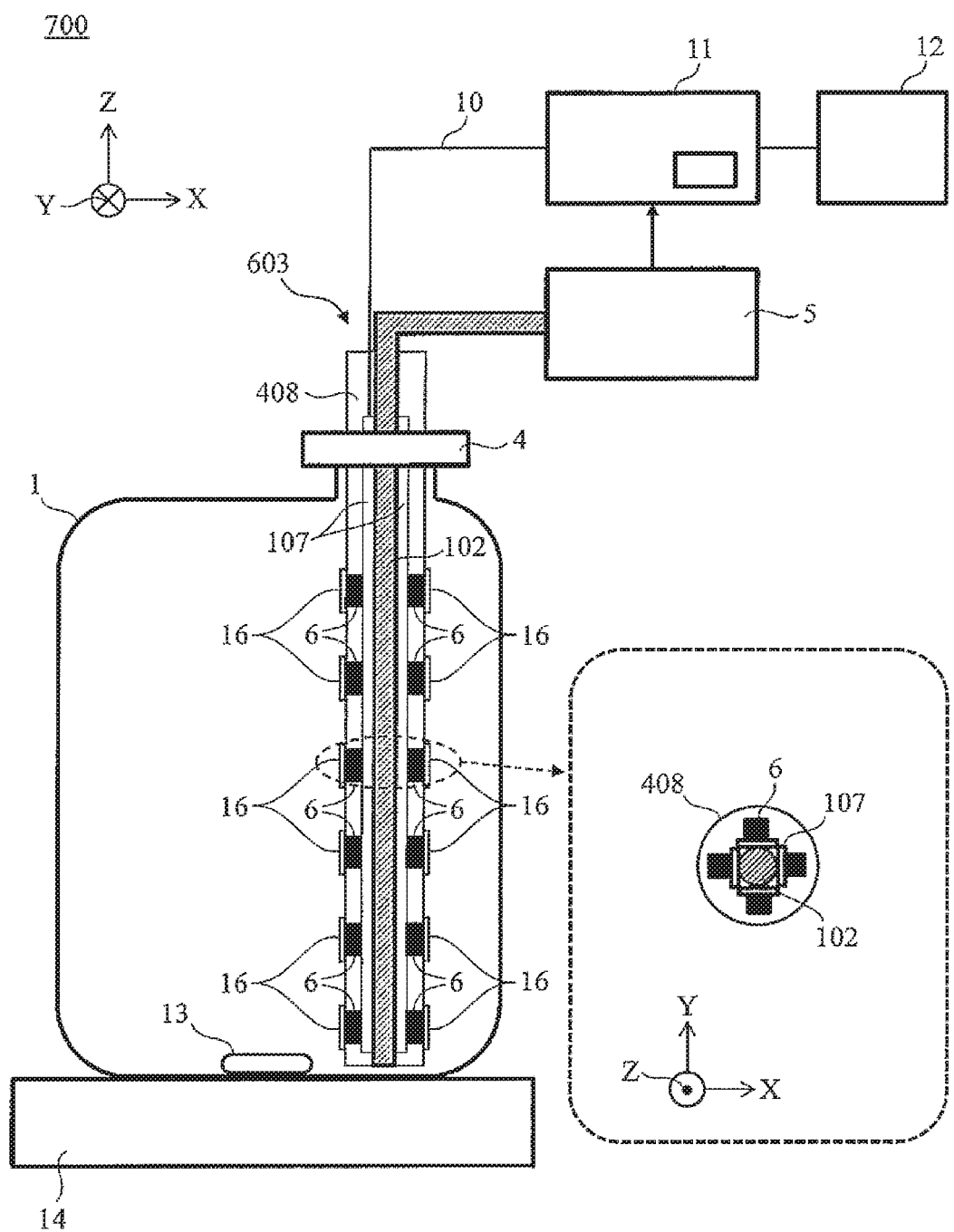
FIG. 8 is a diagram illustrating a schematic configuration of an automatic analyzer according to a ninth embodiment.

FIG. 8 illustrates a schematic configuration of an automatic analyzer 700 according to a ninth embodiment. In FIG. 8, corresponding sections to those in FIG. 4 are denoted by same or corresponding reference characters. The automatic analyzer 700 uses a sterilization mechanism 603. While a configuration is adopted such that the sterilization mechanism and the suction nozzle 2 are separate members and are fixed to the fixed section 4 in the preceding embodiments, the sterilization mechanism 603 is configured integrally with a suction nozzle.

Specifically, a configuration is adopted such that the sterilization mechanism 603 is attached to a surface of a suction nozzle 102. Integrating the sterilization mechanism 603 with the suction nozzle 102 makes it possible not only to simultaneously pull out or insert the sterilization mechanism 603 and the suction nozzle 102 at a time of replacement of the reagent but also to facilitate wiping.

In a case of FIG. 8, four ultraviolet LEDs 6 configuring the sterilization mechanism 603 are attached to each of a plurality of height positions of the suction nozzle 102. In a case of the present embodiment, the four ultraviolet LEDs 6 are disposed equidistantly along an outer periphery of the suction nozzle 102. Owing to this, the sterilization mechanism 603 can radiate ultraviolet light generally uniformly in all directions. Needless to say, the number of ultraviolet LEDs 6 disposed at the same height position is not limited to four but may be one, two, three, or equal to or greater than five. It is noted that the ultraviolet LEDs 6 are not necessarily disposed equidistantly and it is desirable to adjust an interval in response to a shape of the reagent container 1 attached to the analyzer body. In addition, disposition of the ultraviolet LEDs 6 may differ depending on the height of the suction nozzle 102.

It is noted that substrates 107 mounting thereon the ultraviolet LEDs 6 are disposed in a space between an accommodation section 408 and the suction nozzle 102. In the case of the present embodiment, the accommodation section 408 is similarly formed with resin or metal. The opening portions are formed at positions facing the ultraviolet LEDs 6 (regions irradiated with the ultraviolet region) in the second accommodation section 408, and the windows 16 are disposed to cover the opening portions. Glass that transmits ultraviolet light is used for the windows 16.

The accommodation section 408 may be formed with a material that transmits ultraviolet light or a material that does not transmit ultraviolet light. Forming the accommodation section 408 with resin or metal makes it possible to reduce a possibility of falsely damaging the sterilization mechanism 603 at a time of replacement of the reagent container 1. In addition, using metal rather than resin can improve heat dissipation performance, and the ultraviolet LEDs 6 can be driven by a higher voltage or current in a range in which the junction temperature of the ultraviolet LEDs 6 does not exceed the maximum absolute rating. When the accommodation section 408 is formed with metal, however, the reagent tends to be warmed. Therefore, resin is used for the accommodation section 408 in a case in which warming of the reagent is to be suppressed.

It is noted that a lower opening end of the suction nozzle 102 is exposed to outside from an opening portion provided in a bottom surface of the accommodation section 408, so that the reagent can be drawn in by suction from the lower opening end. Needless to say, a seal structure or a seal material is used to hermetically close the suction nozzle 102 and the opening portion provided in the bottom surface of the accommodation section 408. Likewise, the windows 16 hermetically close the opening portions provided in the accommodation section 408. The ultraviolet LEDs 6 and the substrates 107 accommodated in the accommodation section 408 are thereby protected from the reagent.

The automatic analyzer 700 configured in this way can reduce blind spots in an ultraviolet light irradiation direction and enhance a sterilization effect, compared with the automatic analyzer 100.

(10) Tenth Embodiment

Figure 9:
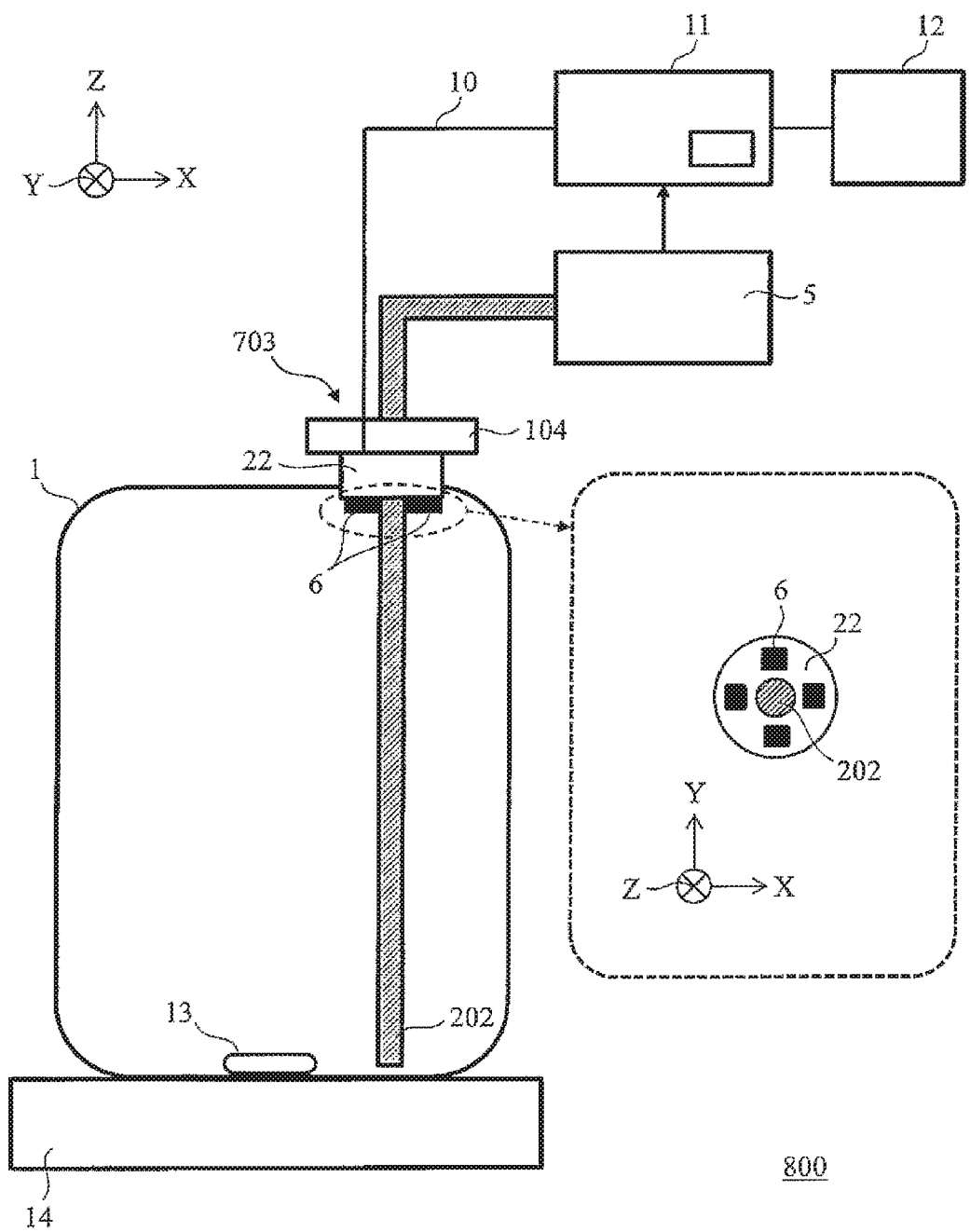
FIG. 9 is a diagram illustrating a schematic configuration of an automatic analyzer according to a tenth embodiment.

FIG. 9 illustrates a schematic configuration of an automatic analyzer 800 according to a tenth embodiment. In FIG. 9, corresponding sections to those in FIG. 1 are denoted by same or corresponding reference characters. The automatic analyzer 800 adopts a configuration of attaching a sterilization mechanism 703 (ultraviolet LEDs 6, a substrate, and a heat dissipation section 22) to a portion of the opening of the reagent container 1. In a case of the present embodiment, the substrate and the heat dissipation section 22 are attached to a lower surface of a fixed section 104, and the substrate and the heat dissipation section 22 are inserted into inside of the opening of the reagent container 1 at a time of attaching the fixed section 104 to the opening of the reagent container 1.

A hole penetrating through each of the fixed section 104, the substrate, and the heat dissipation section 22 is formed, and a suction nozzle 202 is attached to these through-holes. In addition, a plurality of ultraviolet LEDs 6 are disposed on lower surfaces of the substrate and the heat dissipation section 22 in a downward direction. In FIG. 9, four ultraviolet LEDs 6 are attached to the lower surfaces of the substrate and the heat dissipation section 22.

The ultraviolet LEDs 6 are fixed to positions at which the ultraviolet LEDs 6 are kept from contact with the reagent even in a state of fixing the fixed section 104 to the reagent container 1 right after replacement (that is, even in a state in which the liquid level of the reagent within the reagent container 1 is at the highest position). Owing to this, the sterilization mechanism 703 of the present embodiment radiates ultraviolet light from positions above the reagent toward an inner wall surface of the reagent container 1 and the liquid level of the reagent.

In a case of the present embodiment, there is no need to protect the ultraviolet LEDs 6, the substrate, and the heat dissipation section 22 from the reagent. However, in a case in which vibration is applied to the reagent container 1 in a state in which the reagent and the sterilization mechanism 703 are present within the reagent container 1, the reagent possibly contacts the sterilization mechanism 703. Therefore, the sterilization mechanism 703, the substrate, and the heat dissipation section 22 may be protected from the reagent.

It is noted that the suction nozzle 202 may be either fixed to the fixed section 104 integrally with the sterilization mechanism 703 or separable from the sterilization mechanism 703. In addition, part of or all of the functions of the control section 11 may be mounted in one of or both of the substrate and the heat dissipation section 22.

In the case of the present embodiment, most of the heat from the ultraviolet LEDs 6 is released into the air via the substrate and the heat dissipation section 22. Owing to this, it is possible to suppress an increase in the junction temperature of the ultraviolet LEDs 6 and reduce the probability that the junction temperature exceeds the absolute maximum rating specified by the specifications. As a result, it is possible to extend the lives of the ultraviolet LEDs 6 and reduce a failure occurrence frequency.

It is desirable that the substrate and the heat dissipation section 22 are formed with metal having high thermal conductivity such as aluminum, copper, or stainless steel. In addition, a heat sink structure may be adopted for the substrate and the heat dissipation section 22. Furthermore, the fixed section 104 may have a heat dissipation function. Moreover, similarly to the other embodiments, a temperature sensor such as a thermistor may be disposed near the ultraviolet LEDs 6, and the control section 11 may indirectly measure the junction temperature of the ultraviolet LEDs 6. In this case, the control section 11 controls any of or some of the current, the voltage, and the current-carrying time for the ultraviolet LEDs 6 on the basis of the measured junction temperature, thereby exercising control such that the junction temperature of the ultraviolet LEDs 6 does not exceed the absolute maximum rating.

Using the automatic analyzer 800 configured in this way makes it possible to achieve both the inhibition of the change in the properties of the reagent and the propagation of microorganisms and the sterilization of the reagent similarly to the preceding embodiments. In addition, it is possible to minimize time and labor involved in the reagent transfer work and degradation in a quality of the reagent since the reagent container 1 is used in a state of being attached to the automatic analyzer 800 as it is.

(11) Other Embodiments

The present invention is not limited to the embodiments described above but encompasses various modifications. For example, the abovementioned embodiments have been described in detail for describing the present invention so that the present invention is easy to understand; however, the present invention does not always include all the configurations described. In addition, a part of the configuration of a certain embodiment may be replaced by the configuration of another embodiment. Furthermore, the configuration of another embodiment can be added to the configuration of a certain embodiment. Moreover, part of the configuration of each embodiment can be deleted.

DESCRIPTION OF REFERENCE CHARACTERS

1: Reagent container
2, 102, 202: Suction nozzle
3, 103, 203, 303, 403, 503, 603, 703: Sterilization mechanism
4, 104: Fixed section
5: Analysis section
6: Ultraviolet LED
7, 107: Substrate
8, 108, 208, 308, 408: Accommodation section
9: Cap section
10: Interconnection
11: Control section
11A: Storage section
12: Display section
13: Stirrer
14: Magnetic stirrer
15: Ultraviolet lamp
16: Window
17: First accommodation section
18: Cap section of first accommodation section
19, 119: Second accommodation section
20: Cap section of second accommodation section
21: Adiabatic section
22: Substrate and heat dissipation section
100, 200, 300, 400, 500, 600, 700, 800: Automatic analyzer All the publications and patent documents cited in the present specification are incorporated into the present specification by referring thereto.

The invention claimed is:
1. An automatic analyzer comprising:
a sterilization mechanism including a housing and an ultraviolet LED disposed inside the housing, the ultraviolet LED being disposed inside a container in which a reagent is held and emitting ultraviolet light to sterilize the reagent, wherein the housing is detachably attached via a fixed section to a mouth of the container;
a suction nozzle that is detachably attached, together with the sterilization mechanism, via the fixed section to the mouth of the container, the suction nozzle being configured to suction a first portion of the reagent from the container;
an analysis apparatus configured to receive the first portion of the reagent from the suction nozzle and to detect an amount of reagent in the container, or a liquid level detector disposed in the container and configured to detect the amount of the reagent in the container; and
a controller operatively connected to the analysis apparatus or the liquid level detector, based on which of the analysis apparatus and the liquid level detector detects the amount of the reagent in the container, and programmed to exercise variable control over an irradiation light intensity of the ultraviolet light emitted by the ultraviolet LED;
wherein the controller exercises control over the irradiation light intensity of the ultraviolet light based on the amount of the reagent remaining in the container after the first portion of the reagent has been removed from the container by the suction nozzle.
2. The automatic analyzer according to claim 1, wherein the controller obtains the amount of the reagent remaining in the container based on either a number of times of analysis indicated by the analysis apparatus or a liquid level height detected by the liquid level detector.
3. The automatic analyzer according to claim 1, wherein the controller exercises control over the irradiation light intensity of the ultraviolet light through control over both or either one of an illuminance of the ultraviolet light and irradiation time.
4. The automatic analyzer according to claim 1, wherein the ultraviolet LED emits the ultraviolet light at a wavelength from 180 to 350 nm.

5. The automatic analyzer according to claim 1, wherein the controller controls the irradiation light intensity of the ultraviolet light through control over any of a current supplied to the ultraviolet LED, a voltage, and current-carrying time.

6. An automatic analyzer comprising:
a sterilization mechanism including a housing and an ultraviolet LED disposed inside the housing, the ultraviolet LED being disposed inside a container in which a reagent is held and emitting ultraviolet light to sterilize the reagent, wherein the housing is detachably attached via a fixed section to a mouth of the container;
a suction nozzle that is detachably attached, together with the sterilization mechanism, via the fixed section to the mouth of the container, the suction nozzle being configured to suction a first portion of the reagent from the container;
an analysis apparatus configured to receive the first portion of the reagent from the suction nozzle and to detect an amount of reagent in the container, or a liquid level detector disposed in the container and configured to detect the amount of the reagent in the container;
a controller operatively connected to the analysis apparatus or the liquid level detector, based on which of the analysis apparatus and the liquid level detector detects the amount of the reagent in the container, and programmed to exercise variable control over an irradiation light intensity of the ultraviolet light emitted by the ultraviolet LED; and
a magnetic stirrer disposed outside of the container that drives a stirring bar loaded into the container, from outside of the container;
wherein the controller exercises variable control over the irradiation light intensity of the ultraviolet light based on the amount of the reagent remaining in the container after the first portion of the reagent has been removed from the container by the suction nozzle.

7. The automatic analyzer according to claim 1, wherein the housing of the sterilization mechanism makes the ultraviolet LED waterproof from the reagent and includes a region transmitting the ultraviolet light emitted from the ultraviolet LED.

8. An automatic analyzer comprising:
a sterilization mechanism including a housing and a plurality of ultraviolet LEDs disposed inside the housing, the plurality of ultraviolet LEDs being disposed inside a container in which a reagent is held and emitting ultraviolet light to sterilize the reagent, wherein the housing is detachably attached via a fixed section to a mouth of the container;
a suction nozzle that is detachably attached, together with the sterilization mechanism, via the fixed section to the mouth of the container, the suction nozzle being configured to suction a first portion of the reagent from the container;
an analysis apparatus configured to receive the first portion of the reagent from the suction nozzle and to detect an amount of reagent in the container, or a liquid level detector disposed in the container and configured to detect the amount of the reagent in the container; and
a controller operatively connected to the analysis apparatus or the liquid level detector, based on which of the analysis apparatus and the liquid level detector detects the amount of the reagent in the container, and programmed to exercise variable control over an irradiation light intensity of the ultraviolet light emitted by the plurality of ultraviolet LEDs;
wherein the plurality of ultraviolet LEDs includes a plurality of groups of ultraviolet LEDs, each of the groups being disposed to surround the suction nozzle at a different height position of the suction nozzle.

9. The automatic analyzer according to claim 1, wherein the sterilization mechanism further includes a second housing that accommodates the housing; and a heat insulation section that is disposed between the housing and the second housing.

10. An automatic analyzer comprising:
a sterilization mechanism including a housing and an ultraviolet LED disposed inside the housing, the ultraviolet LED being disposed inside a container in which a reagent is held and emitting ultraviolet light to sterilize the reagent, wherein the housing is detachably attached via a fixed section to a mouth of the container;
a suction nozzle that is detachably attached, together with the sterilization mechanism, via the fixed section to the mouth of the container;
an analysis apparatus configured to add the reagent absorbed by suction from the container via the suction nozzle and to detect an amount of reagent in the container, or a liquid level detector disposed in the container and configured to detect the amount of the reagent in the container; and
a controller operatively connected to the analysis apparatus or the liquid level detector, based on which of the analysis apparatus and the liquid level detector detects the amount of the reagent in the container, and programmed to exercise variable control over an irradiation light intensity of the ultraviolet light emitted by the ultraviolet LED; wherein
the ultraviolet LED includes a plurality of ultraviolet LEDs arranged in a depth direction of the container and attached to the container, and
the controller exercises control in such a manner as to turn off the ultraviolet LEDs located above a liquid level of the reagent detected by the liquid level detector or reduce a light intensity of the ultraviolet LEDs.

11. The automatic analyzer according to claim 1, wherein the ultraviolet LED includes a plurality of ultraviolet LEDs,
the sterilization mechanism has a temperature sensor that measures a junction temperature of the ultraviolet LEDs either directly or indirectly, and
the controller exercises control over any of a current supplied to the ultraviolet LED, a voltage, and current-carrying time on the basis of the measured junction temperature.

12. The automatic analyzer according to claim 1, wherein the controller indicates on a display screen whether appropriate sterilization has been executed or detection of an abnormality has occurred.

* * * * *